(12) United States Patent
Haverinen et al.

(10) Patent No.: US 6,623,555 B1
(45) Date of Patent: Sep. 23, 2003

(54) COMPOSITE PRECIPITATED CALCIUM CARBONATE/SILICON COMPOUND PIGMENT AND METHOD OF MAKING SAME

(76) Inventors: Jukka P. Haverinen, Patruunantie 8, FIN-49400 Hamina (FI); Eero H. Seuna, Paationkatu 7, FIN-49410 Poitsila (FI); Henrik Fordsmand, Trongaardsparken 47, DK-2800 Lyngby (DK)

( * ) Notice: Subject to any disclaimer, the term of this patent is extended or adjusted under 35 U.S.C. 154(b) by 0 days.

(21) Appl. No.: 09/584,397

(22) Filed: Jun. 1, 2000

(51) Int. Cl.⁷ .............................. C09C 1/02; C09C 3/06
(52) U.S. Cl. .................. 106/465; 106/464; 423/430; 423/432
(58) Field of Search .................. 106/463, 465, 106/482, 464; 428/404; 423/430, 432

(56) References Cited

U.S. PATENT DOCUMENTS

| | | | |
|---|---|---|---|
| 3,152,001 A | | 10/1964 | Podschus et al. ............ 106/306 |
| 4,167,423 A | | 9/1979 | Williams .................... 106/306 |
| 4,725,318 A | * | 2/1988 | Minayoshi et al. ......... 106/465 |
| 4,781,982 A | * | 11/1988 | Musselman et al. ........ 106/463 |
| 5,000,791 A | | 3/1991 | Tokarz et al. ............... 106/463 |
| 5,164,006 A | | 11/1992 | Chapnerkar et al. ........ 106/465 |
| 5,219,660 A | | 6/1993 | Wason et al. ............... 428/403 |
| 5,262,239 A | | 11/1993 | Wason et al. ............... 428/403 |
| 5,380,361 A | | 1/1995 | Gill ........................... 106/465 |
| 5,584,923 A | | 12/1996 | Wu ............................ 106/464 |
| 5,599,388 A | | 2/1997 | Wu ............................ 106/464 |
| 5,711,799 A | | 1/1998 | Snowden et al. ........... 106/465 |
| 6,136,085 A | * | 10/2000 | Adams, Jr. et al. ......... 106/463 |

FOREIGN PATENT DOCUMENTS

| | | |
|---|---|---|
| EP | 0 356406 | 5/1993 |
| GB | 838903 | 6/1960 |
| GB | 1295264 | 11/1972 |
| GB | 1507745 | 4/1978 |
| JP | 59-206302 | * 11/1984 |
| WO | WO 95/03251 | 2/1995 |
| WO | WO-9739728 | * 10/1997 |

* cited by examiner

*Primary Examiner*—Michael Marcheschi

(57) ABSTRACT

A method of making a composite pigment of precipitated calcium carbonate (PCC) and a silicon compound, in which the resulting composite pigment is endowed with an excellent combination of optical and mechanical properties. Among other things, a PCC/silicate composite pigment made according to this invention imparts increased bulk, light scattering power, porosity and printing properties to paper. The composite pigment material made according to this invention also is very competitive from the standpoint of its production cost. The method for making the composite pigment includes the step of introducing a soluble silicate compound into an aqueous medium containing a precipitate of calcium carbonate formed by carbonation of lime milk, and at a time when the calcium carbonate precipitation reaction has progressed to near completion. Then, an insoluble silicon compound is precipitated upon the precipitated calcium carbonate by carbonation of the reaction mixture in a manner in which the maximum temperature variation of the reaction mixture is kept less than 20° C. The soluble silicate compound is added when the precipitation of the calcium carbonate has reached approximately 90% to less than 100% of completion. Further, the temperature of the reaction mixture during deposition of the silicon compound upon the precipitated calcium carbonate is at least 50° C. or greater, and more preferably is kept between approximately 60 to 100° C.

14 Claims, 11 Drawing Sheets

COMPOSITE PRECIPITATED CALCIUM CARBONATE/SILICON COMPOUND PIGMENT AND METHOD OF MAKING SAME

BACKGROUND OF THE INVENTION

1. Field of the Invention

The invention relates to a unique composite pigment and a method for its preparation, and, more particularly, relates to a composite pigment made by the precipitation of a silicon compound onto precipitated calcium carbonate, and the application of said composite pigment as a filler such as for paper making, a coating pigment, a thickener and/or cleaning agent in toothpaste, a pigment for paint, a conditioner for powders, or as a carrier for liquids or oils.

2. Description of the Related Art

Paper production requires attention to and management of a number of diverse paper quality parameters, such as bulk, opacity, brightness, strength, smoothness, gloss, stiffness, which are important for handability, printability, general appearance and so forth. Fillers are typically used to manipulate one or more of these parameters in a desired manner.

A wide variety of different minerals and synthetic pigments have been investigated and used as fillers in the conventional manufacture of paper. Such paper fillers include, for example, kaolins, calcined clays, titanium dioxide, aluminium trihydrate, ground calcium carbonates, precipitated calcium carbonates, and precipitated silicates. These various types of pigments provide varying overall benefits insofar as the resulting paper qualities and the cost of manufacturing the paper. For example, kaolins are available at low cost, but tend to negatively influence the brightness of the paper compared to the whiter fillers, such as ground marble or PCC. Calcium carbonates, especially PCCs, add scattering power to paper to result in very bright papers, and also permit reductions in production costs. However, it tends to be a challenge to improve other paper properties such as bulk where PCC is the filler, such as by using coarser PCC particles of a given morphology, without adversely impacting and compromising scattering power. Calcined clays and precipitated silicates result in very bright papers with a high opacity and good bulk, but have the disadvantage of being relatively expensive as compared to competing paper fillers.

Consequently, one prior approach has been to combine usage of two or more different types of particulate fillers in paper manufacture in order to combine the respective advantages and/or compensate for the respective drawbacks of the different fillers being added. However, the use of multiple fillers tends to increase the risk of product variability, and also tends to increase material costs and material handling requirements for paper manufacture.

As an alternate approach, the use of composite pigments per se as fillers for paper manufacture has been suggested. Namely, methods have been suggested for manufacturing composite pigment particles constituted by precipitated calcium carbonate and silicon dioxide, and the application of such composite pigments as fillers for the manufacture of paper. For example, WO 95/03251 discloses a process wherein milk of lime ("lime milk") and an aqueous solution of sodium silicate is mixed, whereafter a mixed pigment comprising calcium carbonate and silica is precipitated simultaneously by injection of a gas containing carbon dioxide into the mixture until the pH falls to 7 or below. The molar ratio $SiO_2/CaO$ is kept at 3.6. The resulting compound pigment is used as filler in paper and purportedly has good optical characteristics. EP 356406 discloses a process wherein a PCC is coated with a zinc silicate in order to make it acid resistant. The zinc silicate is precipitated onto the PCC by a process route wherein a sodium silicate solution and a zinc chloride solution are simultaneously admixed into the PCC suspension and wherein the zinc chloride solution is substituted by a sulphuric acid solution in the latter part of the reaction. GB 1295264 discloses a process wherein calcium silicate is precipitated onto chalk by admixing of a sodium silicate solution into a chalk suspension and stirring it for 30 minutes. The resulting pigment is acid resistant and can be used as filler for "alum" sized paper. U.S. Pat. No. 5,164,006 discloses a process wherein a silicate is precipitated onto calcium carbonate, e.g. PCC, to prepare an acid resistant calcium carbonate pigment. The U.S. Pat. No. 5,164,006 patent teaches a two stage pH-reduction process for making the pigment wherein the first stage comprises addition of a sodium silicate solution to a calcium carbonate suspension which has a temperature in the range of about 75° C. to 80° C., and a high amount of excess (unreacted) calcium hydroxide (2–5 g/L excess) and a corresponding high pH (11–12), and reducing the pH to the range of 10.2–10.7 by addition of carbon dioxide gas. Then, in a second stage, the reaction mixture is cooled to about 20° C. to 35° C. and the pH is further reduced to 7.5–8.0 by adding zinc chloride. Other examples in the description of U.S. Pat. No. 5,164,006 describe a comparative process for making the composite pigment, where the two-stage pH reduction instead is accomplished by addition of carbon dioxide in both stages where the reaction temperature is precipitously lowered from 80° C. to 25° C. in the middle of the silicon deposition reaction and before performing the second pH-reduction stage of the process.

As generally understood in the field, calcium carbonate may precipitate in three distinct polymorphs: calcite, aragonite and vaterite. The thermodynamically stable product is calcitic PCC. Aragonite and vaterite are both metastable compounds. Normally, vaterite transforms into calcite within a few hours to a day unless special measures have been taken to stabilize the vaterite polymorph. Aragonite, on the other hand, has, for all practical purposes, an infinite shelf life under normal temperatures and pressures. Aragonite precipitates into acicular needles. Calcite on the other hand may precipitate into various crystal habits comprising scalenohedrons and rhombohedrons. In practice, perfect crystal habits are almost only seen in small-scale precipitations performed under well-controlled conditions in the laboratory. Precipitations on a larger scale such as industrial precipitations tend to produce imperfect crystal habits, which may be intermediate in nature, or have defects such as rounded corners. The individual crystals will typically be assembled in aggregates or agglomerates.

Although not related to paper manufacture per se, certain composite calcium carbonate/silicate pigments and methods for manufacture of these also have been proposed for the rubber and polymer industry. Rubber reinforcing agents typically require a high specific surface area (BET). High surface area pigments, namely pigments having surface areas greater than 30 $m^2/g$ generally are not suitable for paper manufacturing applications at high loading levels because the high surface areas frustrate the ability to provide a filterable pigment composition for paper manufacturing applications.

GB 838903 discloses a process wherein a calcium silicate is precipitated with a PCC. The silicate solution may be added before, during or after the precipitation of the PCC. However, a starting temperature of 15° C. for the carbonation reaction used in the PCC pigment synthesis can be expected to implicitly result in a high surface area PCC product of 20–30 $m^2/g$ BET (see FIG. 2 discussion infra). Further deposition of silicates on the PCC particles would only further increase the surface area. Consistently, the background descriptions of GB 838903 indicate that calcium carbonates used for rubber reinforcement are very small, typically 50–100 nm, and that even smaller particles of 30–50 nm are preferred. Such small pigment particles will by nature have relatively high surface areas. U.S. Pat. No. 3,152,001 discloses a process where a fine calcium silicate is precipitated onto a fine PCC by admixing sodium silicate and calcium chloride solutions into the PCC slurry. The products are stated to have specific surface areas above 50 $m^2/g$. U.S. Pat. No. 4,167,423 discloses a process where freshly precipitated metal silicates are admixed with wet ground calcium carbonates. The metal silicates attach to the calcium carbonate in such a way that they can be used as basis for further reaction with organosilane compounds.

SUMMARY OF THE INVENTION

The present invention relates to a unique approach for making a composite pigment of precipitated calcium carbonate (PCC) and a silicon compound, in which the resulting composite pigment is endowed with an excellent combination of optical and mechanical properties. Among other things, a PCC/silicate composite pigment made according to this invention imparts improved bulk, light scattering power, porosity, roughness, and printing properties to paper. The composite pigment material made according to this invention also is very competitive from the standpoint of its production cost.

As a general embodiment, the present invention relates to a method for making a composite pigment wherein a soluble silicate compound is introduced into an aqueous medium containing a precipitate of calcium carbonate formed by carbonation of lime milk, and at a time when the calcium carbonate precipitation reaction has progressed to near completion. Then, an insoluble silicon compound is precipitated upon the precipitated calcium carbonate by carbonation of the reaction mixture in a manner in which the maximum temperature variation of the reaction mixture is kept less than 20° C. In one preferred embodiment, the soluble silicate compound is added when the precipitation of the calcium carbonate has reached approximately 90% to less than 100% of completion, as calculated as a ratio of the original molar amount of calcium supplied via the calcium hydroxide reactant that has been consumed so far to form the calcium carbonate intermediate product divided by the original molar amount of calcium. In another preferred embodiment, the temperature of the reaction mixture during deposition of the silicon compound upon the precipitated calcium carbonate is at least 50° C. or greater, and more preferably is kept between approximately 60 to 100° C., and more preferably between 70 to 90° C.

By controlling the precipitation reaction conditions according to the above-mentioned protocols, the inventive method is conducted within a unique processing envelope so as to achieve a composite precipitated calcium carbonate/silicon compound pigment having a special morphology and constitution, which is well-suited and versatile for use as a paper filler, a paint pigment, and the like. For paper filler or pigment applications, the composite pigments of this invention can be provided in aqueous slurry form or dry form. The aqueous slurry forms of the inventive composite pigments also optionally can include various other kinds of additives conventionally used in compositions for papermaking. Also, if dried, the inventive pigment solids can be used in a dry, flowable particulate form for incorporation into a dentifrice as a thickener or cleaning agent, or as a carrier for oils and liquids, and the like.

Other aspects and preferred embodiments will be apparent from the following detailed description of the invention.

BRIEF DESCRIPTION OF DRAWINGS

Reference is now made to the accompanying drawings, in which.

DETAILED DESCRIPTION OF THE PREFERRED EMBODIMENTS

The present invention relates to formation of composite PCC/silicon compound pigments by a processing route requiring appropriate attention, control and finesse be given at both reaction levels of a two-tiered composite pigment formation procedure, namely at both an initial PCC formation level and at a subsequent silicon compound deposition reaction level.

In the first reaction tier of the inventive method for making the desired composite pigment, a PCC precipitation reaction is controlled to yield PCC particles, as an intermediate product, having a desirable morphology. For this reaction tier, the sensitivity of the calcium carbonate precipitation reaction outcome to the reaction temperature is shown by the following discussions and referenced figures.

In this regard, it first will be appreciated that the precipitation of calcium carbonate by carbonation of an aqueous calcium hydroxide suspension (i.e., lime milk) may follow one of several distinct reaction pathways leading to different polymorphs and crystal habits of calcium carbonate. Again, the factor which ostensibly has the predominant influence on the reaction pathway encountered is the reaction temperature.

For instance, and although not used in the present invention, if a starting temperature ("T-start") in the range from 0° C. to about 6° C. were used for the PCC precipitation reaction, the initial PCC precipitate would be calcium carbonate hexahydrate, $CaCO_3 6H_2O$, which is also known as the mineral ikaite, which during the reaction will transform into colloidal PCC which is agglomerates of very small crystals and has a high specific surface area (BET) typically above 15 $m^2/g$.

Figure 1:
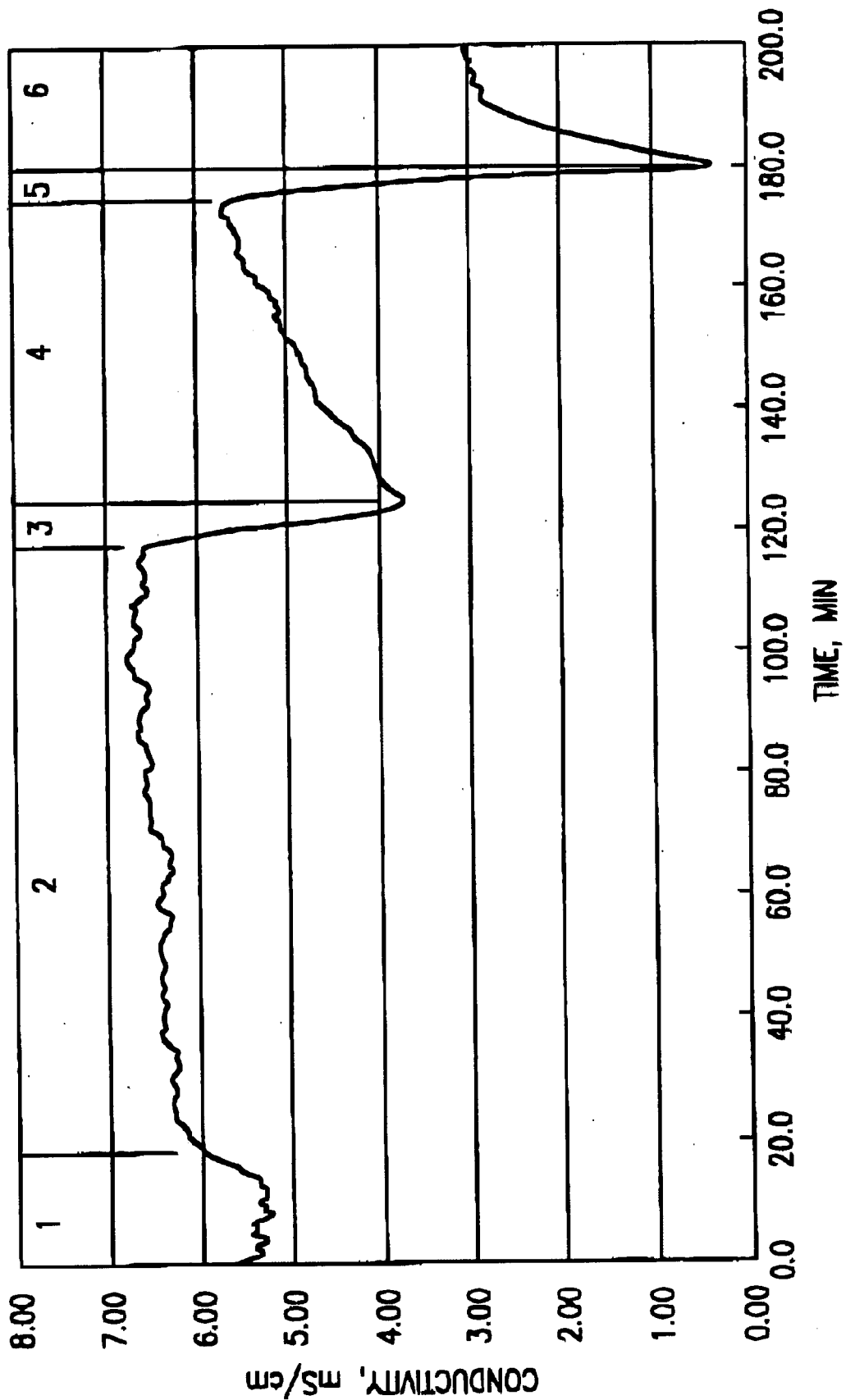
FIG. 1 is a graph showing the conductivity, mS/cm, of an aqueous reaction mixture, in which calcium carbonate is being precipitated by carbonation of lime milk, as a function of reaction time for a starting reaction temperature of within 8–14° C.

Alternatively, if a T-start for the PCC precipitation reaction was used in the range from about 8° C. to about 14° C., the initial precipitate would be an amorphous calcium carbonate gel (ACC) that coats the suspended, undissolved calcium hydroxide particles and thereby reduces the dissolution rate of calcium hydroxide. This reduced dissolution rate for calcium hydroxide causes the aqueous phase to be undersaturated with calcium hydroxide, which can be seen as the reduction in the conductivity in period 1 in FIG. 1. Such an ACC gel transforms after a certain amount of time into nuclei of basic calcium carbonate crystals (BCC, $2CaCO_3 Ca(OH)_2 1.5H_2O$). The crystallization in the gel layer removes the hindrance for the dissolution of calcium hydroxide and the aqueous phase becomes saturated with calcium hydroxide resulting in the increase in conductivity at the end of period 1 in FIG. 1. The BCC crystals grow until essentially all of the calcium hydroxide has dissolved, and during this period the conductivity of the slurry is virtually constant as seen in period 2 in FIG. 1. Then, the aqueous phase again becomes undersaturated with calcium hydroxide when essentially all of the calcium hydroxide has been dissolved, resulting in a drop in conductivity as seen in period 3 in FIG. 1. The aqueous phase becomes, at a certain point of time, undersaturated with respect to BCC which then starts to dissolve and transform into calcitic PCC which can be seen as a gradual increase in conductivity during period 4 in FIG. 1. The conductivity drops steeply when essentially all of the BCC has dissolved and the predominant part of the calcium has been precipitated as calcium carbonate as can be seen in period 5 in FIG. 1. The pH of the aqueous phase drops steeply when all the BCC has dissolved and the predominant part of the calcium has been precipitated as calcium carbonate and this pH drop results in that the magnesium hydroxide present with the calcium carbonate transforms into the more soluble magnesium bicarbonate creating a higher conductivity as seen in period 6 in FIG. 1. In this FIG. 1 process scheme, calcium hydroxide precipitates as BCC, not as PCC, consequently all solid calcium hydroxide is consumed in Period 3. In the PCC forming Period 4 there is no solid calcium hydroxide present; PCC is precipitated from BCC. In Period 5 all BCC has been consumed leading to the pH drop. If a T-start for the PCC precipitation reaction was used in the range from about 8° C. to about 14° C., the PCC ultimately formed would be agglomerates of crystals which are of predominantly rhombohedral character with relatively low surface areas, typically 2–12 $m^2/g$, more typically 3–10 $m^2/g$ and even more typically 4–8 $m^2/g$.

Figure 2:
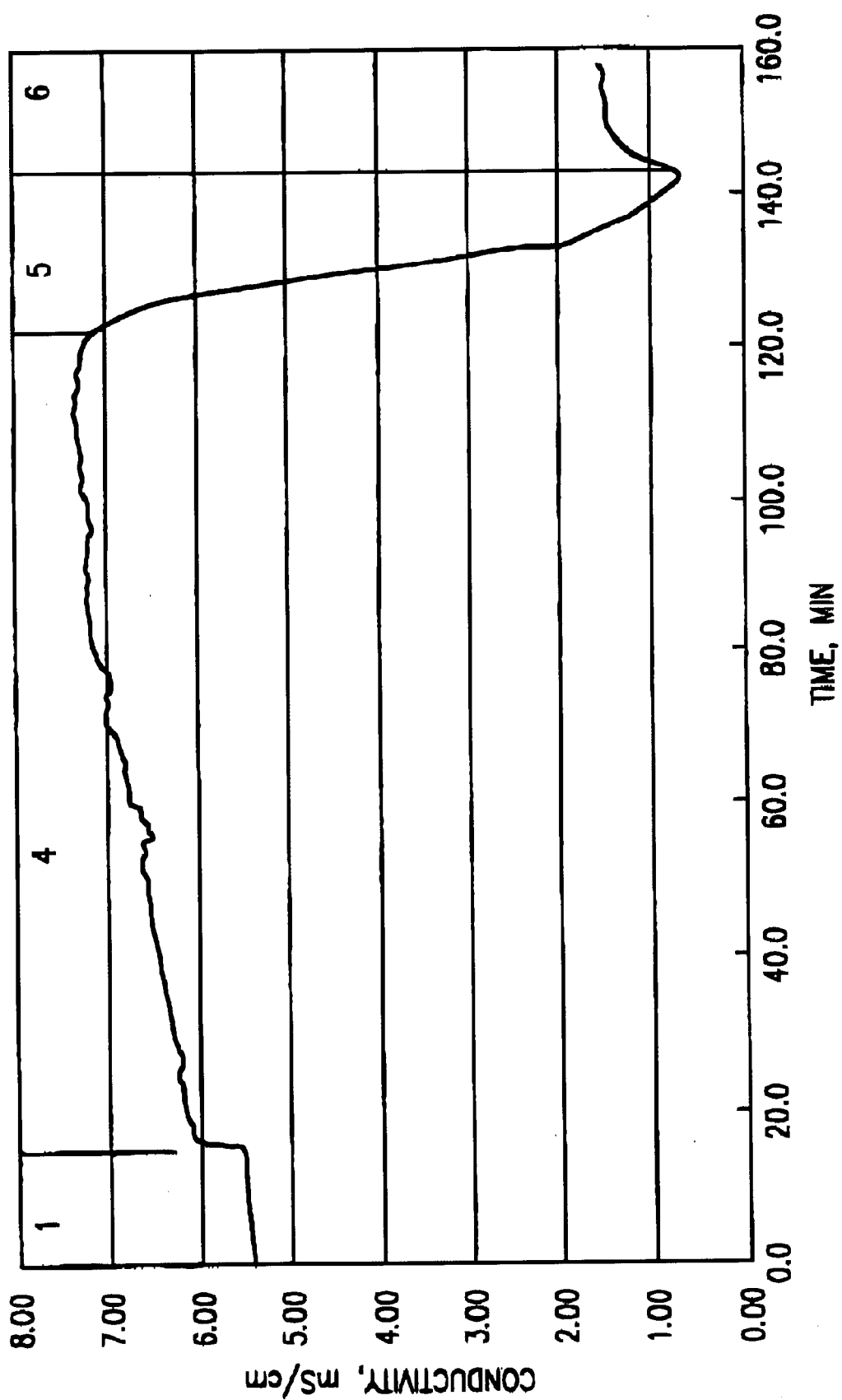
FIG. 2 is a graph showing the conductivity, mS/cm, of an aqueous reaction mixture, in which calcium carbonate is being precipitated by carbonation of lime milk, as a function of reaction time for a starting reaction temperature of within 15–28° C.

Alternatively, if a T-start in the range from about 15° C. to about 28° C. were used, and outside the scope of this invention, the initial precipitate would be an amorphous calcium carbonate gel (ACC) that coats the calcium hydroxide particles and reduces the dissolution rate of calcium hydroxide. This reduced dissolution rate for calcium hydroxide results in that the aqueous phase is undersaturated with calcium hydroxide, which can be seen as the reduction in the conductivity in period 1 on FIG. 2. This ACC gel transforms after a certain amount of time into a large number of nuclei of calcite crystals. The crystallization in the gel layer removes the hindrance for the dissolution of calcium hydroxide and the aqueous phase becomes saturated with calcium hydroxide resulting in the increase in conductivity at the end of period 1 in FIG. 2. The calcite crystals grow until essentially all of the calcium hydroxide has dissolved and during this period the conductivity of the slurry is virtually constant as seen in period 4 in FIG. 2. The aqueous phase becomes undersaturated with calcium hydroxide when essentially all of the calcium hydroxide has dissolved and has been consumed by the reaction, resulting in a drop in conductivity such as seen in period 5 in FIG. 2. Magnesium hydroxide soon thereafter dissolves as described above in connection with FIG. 1 into magnesium bicarbonate creating a higher conductivity as seen in period 6 in FIG. 2. The PCC formed by such a process where T-start for the precipitation of PCC is about 15° C. to about 28° C. is dense agglomerates of very small crystals which are of predominantly rhombohedral character with high surface areas, typically 20–30 $m^2/g$.

Figure 3:
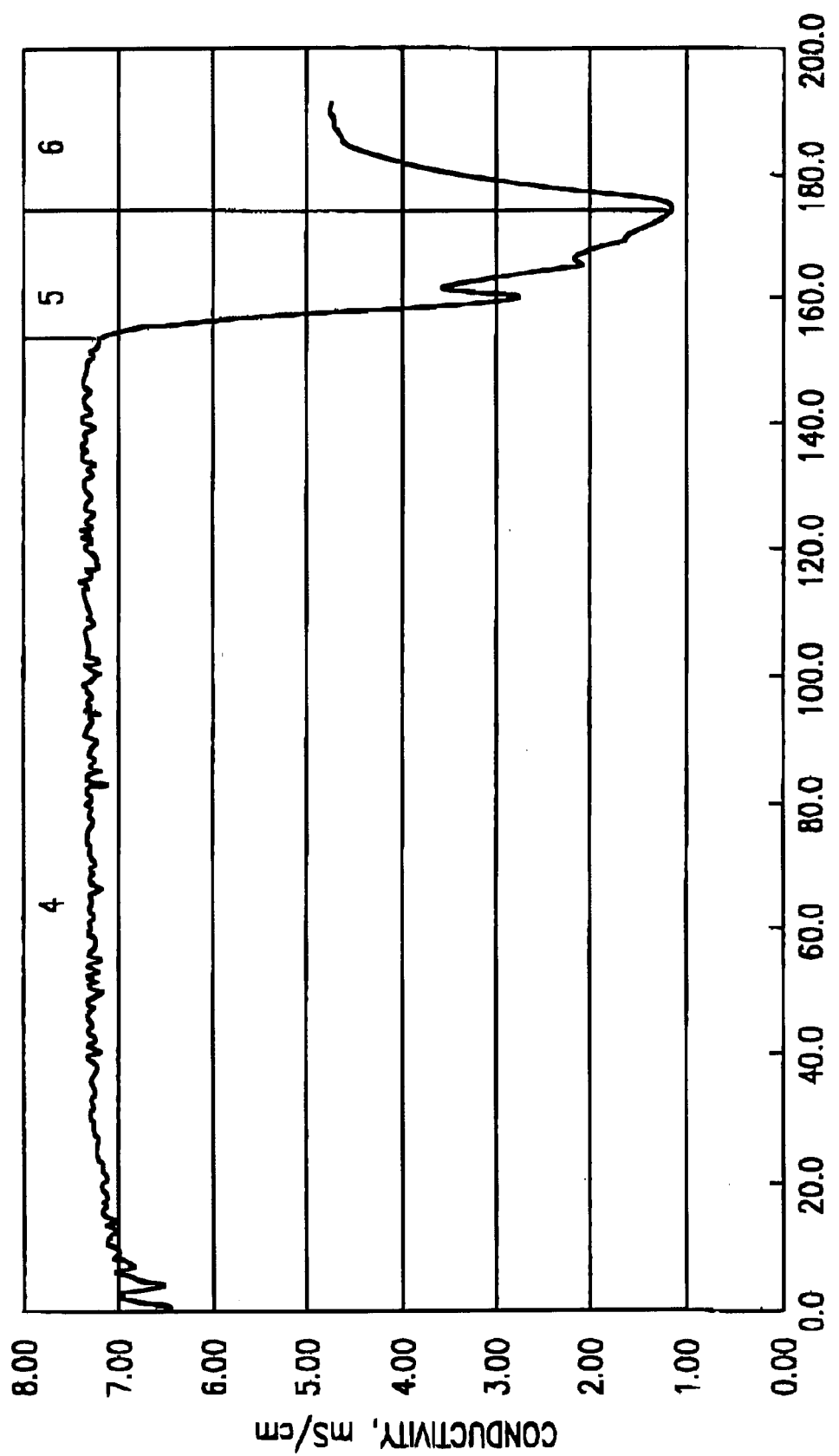
FIG. 3 is a graph showing the conductivity, mS/cm, of an aqueous reaction mixture, in which calcium carbonate is being precipitated by carbonation of lime milk, as a function of reaction time for a starting reaction temperature of above about 30° C.

Alternatively, if a T-start above about 30° C. were used, virtually no ACC is formed and calcitic PCC precipitates directly from the calcium hydroxide with the conductivity being virtually constant as long as there remains solid suspended calcium hydroxide as can be seen in period 4 in FIG. 3. The direct precipitation of PCC could be seeded by addition of calcite nuclei before start of the carbonation. The aqueous phase becomes undersaturated with calcium hydroxide when essentially all of the calcium hydroxide has dissolved and has been consumed by the reaction, resulting in a drop in conductivity as seen in period 5 in FIG. 3. Magnesium hydroxide soon thereafter dissolves as described above in connection with FIG. 1 into magnesium bicarbonate creating a higher conductivity as seen in period 6 in FIG. 3. The PCC formed by such a scenario where T-start for the precipitation of PCC is above about 30° C. are in the form of rosette-like aggregates of crystals, which are of predominantly scalenohedral character with relatively low surface areas, typically 2–12 $m^2/g$, more typically 3–10 $m^2/g$ and even more typically 4–8 $m^2/g$. If a T-start above about 35° C. were used, a competing aragonite reaction pathway is possible in parallel to the calcite reaction pathway resulting in mixtures of rosette-like aggregates of calcite crystals and aggregates of acicular needle-like aragonite crystals. This aragonite reaction pathway can be suppressed by addition of sucrose to the reaction mixture before carbonation.

The brightness of the PCC may be increased by the addition of sodium thiosulfate ($Na_2S_2O_3$) to the water used for the slaking of the lime or to the milk of lime before carbonation. The effect of this additive is to reduce metallic impurities such as iron and manganese from oxidation state three or higher, where they form strongly coloured impurities, to oxidation state two where they form less coloured impurities. The effect on the brightness of the PCC of the addition of sodium thiosulfate to the slaking water depends on the source of lime.

Figure 4:
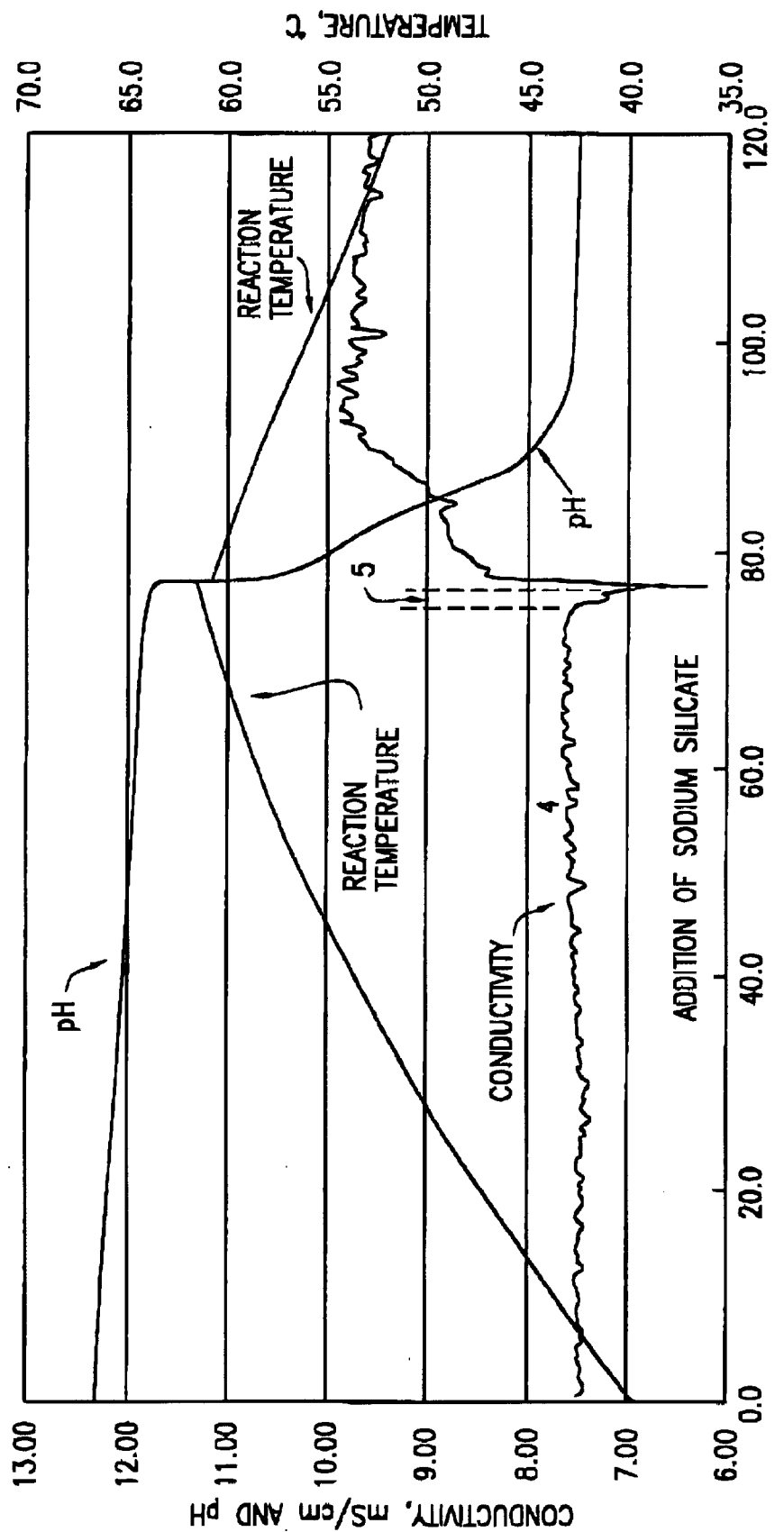
FIG. 4 is a graph showing the conductivity, mS/cm, pH and reaction temperature as a function of reaction time for an aqueous reaction mixture in which a composite precipitated calcium carbonate pigment is made according to an example of this invention.

According to one mode of the practice of the present invention, where a T-start above approximately 35° C., is used for the precipitation of the PCC in a first tier reaction of the inventive method, a conductivity-time plot will be generated such as illustrated in FIG. 4. As with the FIG. 3 illustration, virtually no ACC is formed and the calcitic and/or aragonite PCC precipitate directly from the calcium hydroxide with the conductivity being virtually constant as long as there remains solid suspended calcium hydroxide as can be seen in period 4 in FIG. 4. The aqueous phase ultimately becomes undersaturated with calcium hydroxide when essentially all of the calcium hydroxide has dissolved and has been consumed by the reaction, resulting in a precipitous drop in conductivity as seen in period 5 in FIG. 4. Importantly, the silicon compound deposition procedure is conducted in a manner in which the maximum temperature variation (i.e., the highest minus the lowest temperature measured during the reaction) of the reaction mixture is kept less than 20° C. To accomplish this, the relative concentrations and amounts of the silicon compound forming reactants introduced, such as the water soluble silicon compound, and the carbon dioxide, are sufficiently high enough to permit the silicon compound precipitation to occur at a rate and in an amount that will not be so slow that the reaction mixture will unduly cool off before the reaction has progressed sufficiently; and/or external heating control capability is provided to maintain the reaction mixture at a relatively constant temperature.

According to another mode of the practice of the present invention, where a T-start in the range of from about 8° C. to about 14° C. is used for the precipitation of the PCC in a first tier reaction of the inventive method, the reaction will follow the pathway through ACC and BCC followed by the addition of the soluble silicon compound at the stage where all the BCC has dissolved. Importantly, as above, the silicon compound deposition procedure is conducted in a manner in which the maximum temperature variation (i.e., the highest minus the lowest temperature measured during the reaction) of the reaction mixture is kept less than 20° C.

The above mentioned temperature limits for the PCC forming reactions may be varied somewhat depending on a number of parameters influencing the precipitation process and the resulting crystal habits and sizes. For example, by adding sucrose to the PCC-forming reaction mixture including the lime milk to be carbonated, the production of pure calcite is permitted even where T-start is as high as up to about 50° C. or higher. The addition of sucrose to the PCC-forming reaction mixture suppresses aragonite formation. Also, the direct precipitation of the PCC can be facilitated by the use of seeding techniques by addition of calcite nuclei to the aqueous medium before the start of carbonation. Other parameters that effect the temperature limits include the source of the burnt lime used for manufacturing the calcium hydroxide suspension, the reaction parameters for manufacturing the calcium hydroxide suspension (the slaking process), the solids content in the carbonation reaction mixture, the aeration during carbonation, the carbon dioxide content in the gas used for carbonation, the mixing intensity as defined by the size and shape of the stirrer and the stirring speed, impurities in the burnt lime, the flue gas or the process water, as well as additives added to the process. With these general concepts in mind regarding the nature of the PCC-forming reaction, the specific methodology of this invention is now described in even greater detail below.

According to the present invention, a soluble silicate compound is added to the PCC reaction at a time near the end of the calcium carbonate precipitation reaction and then the reaction temperature is carefully monitored such that the silicon compound deposition upon the raw PCC particles, which is induced by carbonating the reaction mixture, occurs at a relatively high and constant temperature. Preferably, the time for addition of the soluble silicate compound reactant is made during the time period where essentially all calcium hydroxide and basic calcium hydroxide have dissolved and substantially all, e.g., 90% up to 100%, of the calcium has precipitated as calcium carbonate (e.g., compare to period 5 in FIGS. 1–3, with the pronounced reduction in the conductivity of the reaction suspension). That is, the soluble silicate compound is added when the precipitation of the calcium carbonate has reached approximately 90% to 100% of completion, as calculated as a ratio of the original molar amount of calcium supplied via the calcium hydroxide reactant that has been consumed so far to form the calcium carbonate intermediate product divided by the original molar amount of calcium. As a general rule of thumb for this invention, these criteria typically will be met if the soluble silicate compound reactant is added within about 10 minutes before completion of the PCC-forming reaction. The progress of the reaction around 100% completion can be deduced by monitoring the conductivity curve and looking for the steep drop in conductivity at 100% completion. The running of experimental control runs (i.e., the same protocol except without adding the silicate reactant) can be used to empirically provide information on the predicted completion times of the PCC-forming reaction alone for a given set of reaction conditions. Alternatively, the introduction of the soluble silicate could be started during the after-carbonation period (corresponding to period 6 in FIGS. 1–3). Preferably, the PCC and silicate precipitations reactions are slightly overlapped in this manner, although the invention is not thought to be limited to that scenario.

It will be understood that when the calcium carbonate precipitations are performed as batch processes without regulation of the temperature during the reaction, the energy liberated by the calcium carbonate precipitation reaction will result in an increase in the temperature of the suspension to higher than T-start during the course of the PCC precipitation process. Therefore, the reaction mixture often will not require any external heating between the times of initiating the PCC-forming reaction and later initiating the silicon compound deposition in the practice of this invention. However, external control of the reaction mixture temperature at the point of silicate addition and during the final part of the silicate deposition reaction to control silicate precipitation can optionally be practiced. For example, the reaction mixture temperature can be increased to 70 to 90° C. by heating the contents of the reaction vessel using conventional heating means for that purpose in order to control physical and functional properties of precipitated silicate coating like specific surface area, pore volume, zetapotential or silicate structure in general.

The contents of the reactor vessel are stirred and agitated thoroughly and continuously throughout the PCC-forming and silicate deposition reactions to ensure a substantially uniform temperature, reactant dispersion, and slurry dispersion are provided throughout the reaction mixture at any given time.

Any type of PCC, which has a specific surface area after the BET method (Brunauer, Emmet, Teler, DIN 66131) below 15 $m^2/g$, e.g. 2–12 $m^2/g$, e.g. 3–10 $m^2/g$, e.g. 4–8 $m^2/g$, may be used as basis for the present invention. The precipitation of the silicon compound onto the PCC will increase the BET to typically 5–25 $m^2/g$, e.g. 10–25 $m^2/g$ for PCC types with BET values as stated above. If the BET value for the PCC that is used as basis for the invention is above 15 $m^2/g$, then the BET of the resulting product will be above 30 $m^2/g$, typically above 50 $m^2/g$. Such high surface areas are ill-suited for many applications, especially in many paper applications.

More specifically, the PCC types, which may form the basis for the present invention, includes aragonite PCC, calcitic precipitated calcium carbonate in the form of aggregates of calcium carbonate crystals formed by direct transformation of calcium hydroxide into calcium carbonate, and calcitic precipitated calcium carbonate in the form of agglomerates of calcium carbonate crystals formed by transformation of calcium hydroxide into calcium carbonate via an intermediate, basic calcium carbonate. As employed in the present description and claims, the term "direct transformation of calcium hydroxide into calcium carbonate" designates a process, wherein essentially no intermediates such as ACC or BCC are formed. For purposes of this disclosure, "aggregates" means assemblies of crystals, which are bound together by rather strong forces and have grown from a common center. "Agglomerates" are assemblies of crystals, which are bound together by weaker forces and have been assembled after (e.g., by mechanical compaction techniques known in the art) or during the precipitation.

In the present invention, the insoluble silicon compound, which is precipitated onto the PCC to form a composite pigment according to the present invention, preferably is an amorphous, synthetic silicon compound. Suitable silicon compounds include precipitated silicas ($SiO_2$); metal silicates such as an alkaline earth metal silicate (e.g., calcium silicate or magnesium silicate), or alkaline earth metal or alkali metal aluminosilicates; or compound salts of any of the above with calcium carbonate and magnesium carbonate; singly or in combinations thereof. One or more of these silicon compounds are present in composite pigments according to the present invention as a very thin amorphous substantially continuous or intermittent layer on the surfaces of the PCC crystal aggregates. The silicon compound must be derivable from a water soluble precursor.

Various appropriate types of soluble silicon precursor compounds may be used in the present invention as a reactant or precursor material which can be carbonated in aqueous solution to form the insoluble silicon compound precipitate that is deposited upon and attaches to surfaces of the PCC substrate particles. Alkali metal silicate solutions are preferred, such as solutions of sodium silicate ($Na_2O:xSiO_2$, where x is a positive number, indicating that the molar ratio can vary). The amount of soluble silicate compound reactant used according to the present invention is an amount yielding composite pigments having a precipitated silicon compound content in an amount of 0.1 to 16%, preferably 0.4 to 8%, even more preferably 0.8 to 4%, calculated as % weight silica ($SiO_2$) relative to total weight of composite pigment product (dry weight). If the soluble silicate compound is sodium silicate, then the preferred amount of sodium silicate solution added is that providing total sodium silicate in the range of 1–5.5% based on dry weight sodium silicate/dry weight relative to calcium carbonate (i.e., the unmodified PCC intermediate).

The soluble silicate compound will typically be added to the reaction mixture containing the preformed PCC particles without regulation of the temperature of the reaction mixture. In a preferred mode, it is beneficial to adjust the temperature of the reaction mixture to another temperature, typically between 50 and 100° C., preferred between 55 and 80° C., and even more preferably between 60 and 75° C., before addition of the soluble silicate compound.

The carbon dioxide content in the gas used for each carbonation reaction, i.e., the PCC formation and the separate silicon compound deposition, independently may vary between 5 and 100 volume percent, typically between 7 and 40%, preferred between 8 and 30%. It may alternatively be preferred to use virtually pure carbon dioxide with between 90 and 100%.

The composite pigments according to the present invention are cost-effective compared to pure silicate pigments and ready to use without any need for additional treatments such as grinding, washing or dewatering. The only by-product from the reaction is a small amount of sodium bicarbonate, which implies that the pigments will be supplied in dilute sodium bicarbonate solution, which is harmless for most applications. The process is a simple one stage process which does not need intermediate cooling and can easily be applied in satellite production facilities as exemplified by the satellite PCC plants established at many paper mills. Also, using the reaction conditions outlined above and exemplified in the examples below, the synthesis of the silicon-modified PCC composite pigment generally can be completed in less than two hours.

As indicated in the examples below, the use of precipitated calcium carbonate/precipitated silicate composite pigments according to the present invention as fillers in paper has been demonstrated to enhance scattering without any loss in bulk. The use of precipitated calcium carbonate/ precipitated silicate composite pigments according to the present invention as fillers in paper may also have beneficial effects on the coefficient of friction of the resulting paper.

Application of dewatered and dried forms of the precipitated calcium carbonate/precipitated silicate composite pigments made according to the present invention as thickener and/or cleaning agent in toothpaste can benefit from the fact that the PCC part of the composite pigment will act as a thickener whereas the silicate part of the composite pigment will act as cleaning agent. Alternatively, precipitated calcium carbonate/precipitated silicate composite pigments according to the present invention can act as a moisture-controlling and/or anti-caking agent when applied as conditioner for powders. If dried, the precipitated calcium carbonate/precipitated silicate composite pigments according to the present invention also can be used as carrier for liquids and oils, typically liquids and oils which are difficult to handle in pure form. Where the composite pigments are to be used used as a thickener and/or cleaning agent in dentifrice compositions or as a carrier for liquids or oils, additional processing steps of dewatering and drying are needed to separate the composite pigment solids from the aqueous medium in which it has been synthesized in order to provided a usable dried, solid particulate form of said composite pigment. The dewatering and drying of a slurry of composite pigment according to this invention can be accomplished, for example, by conventional means used for those purposes. For instance, after the precipitation reaction, the slurry of composite pigment can be dewatered (e.g., by decanting, centrifuge or pressure filter device, in conjunction with a separate flash tank evaporation), followed by drying the concentrated slurry using any conventional equipment generally used for drying PCC, silica or silicates, e.g., spray drying, nozzle drying, flash drying, rotary wheel drying or oven/fluid bed drying. To decrease the size of composite PCC particles, if desired, conventional comminution processing for PCC can be employed such as involving either an attrition grinding step used before or after dewatering, or, alternatively, the already dried composite pigment product can be ground or milled (e.g., hammer milling, fluid energy or air-jet milling).

The following examples are presented to illustrate the invention but it is not to be considered as limited thereto. In the Examples and throughout the specification, parts are by weight unless otherwise indicated.

EXAMPLES

In the following examples, the following standards and methods were used throughout for determining pigment and paper properties:

| | |
|---|---|
| BET: | DIN 66131 |
| Zeta-potential: | Measured on Acoustosizer from Colloid Dynamics |
| MPS, Acoustosizer: | Measured on Acoustosizer from Colloid Dynamics |
| Oil absorption: | DIN EN ISO 787-5 |
| Bulk: | Scan-P 7:96 |
| Scattering: | ISO 2471 |
| Permeability: | PPS method |
| Strength CD tensile index: | Scan-P 67:93 |
| CD stiffness: | Scan-P 64:90 |

MPS, Sedigraph is measured on a Micromeritics Sedigraph 5100. Samples are prepared by adding an amount of the product corresponding to 2.5 g dry PCC to 80 ml of an 0.05% tetrasodium diphosphate solution. The suspension is stirred for 2 minutes on a magnetic stirrer and submitted to ultrasound using an ultrasonic bath for 15 minutes.

The carbonizing reaction involved in the manufacture of precipitated calcium carbonate/precipitated silicate composite pigment in the following examples were, unless otherwise stated, performed in four liter-capacity cylindrical reactor vessels equipped with baffles, a propeller and a gas dispersion unit.

Example 1

Slaking Procedure 20.5 kg of quick lime (obtained from Beachvilime, Ingersoll, Ontario, Canada) was added to 86.1 kg of 30° C. water in a stirred reactor. 10.2 g $Na_2S_2O_3$ was added to the water before the addition of the quicklime. The reaction mixture was stirred for 30 minutes. The reaction mixture, milk of lime, was then screened on a 250 µm screen.

Carbonating Procedure:

2.4 kg of the above-screened milk of lime was added to a reactor and diluted by addition of 1.8 kg of water. The temperature of the reaction mixture was adjusted to the selected start temperature of 40° C., and 0.14 g sucrose was added.

The propeller was started at a speed of approximately 800 rpm and a mixture of $CO_2$ and atmospheric air containing 25% $CO_2$ was injected through the gas dispersion unit at a rate of 600 L/hr. The reaction was continued until essentially all $Ca(OH)_2$ particles in the milk of lime were consumed, as indicated by a drop in the reaction mixture conductivity being measured. At this point 110 g of sodium silicate solution was added to the reaction mixture and the reaction continued until pH had reached a stable value below 8. The sodium silicate was added as a 37% solution. In the present trial, a sodium silicate with a molar ratio $Na_2O:SiO_2$ of 1:3.3 was used. With this addition, the final composite pigment product contained 3.9 wt % $SiO_2$, calculated as weight $SiO_2$/total weight pigment on a dry basis (or, 6.3% calculated as weight dry water glass/weight PCC).

At the time of sodium silicate addition the reaction mixture had a temperature of 62° C. This temperature was reached as a result of the heat generated by the reaction between $Ca(OH)_2$ and $CO_2$, and no attempts were made to control temperature during the reaction. However, controlling the temperature of the reaction mixture at the point of sodium silicate addition and during the final part of the reaction can be used to control silicate precipitation. The reaction was completed in less than 2 hours. FIG. 4 shows the temperature, conductivity and pH profiles which were measured during the course of reaction.

The product, a precipitated calcium carbonate/precipitated silicate composite, was screened on a 45 µm mesh screen. The undersize (minus) portion was recovered as an aqueous slurry of the composite pigment product, and the over size (plus) portion discarded. The crystalline structure of the composite pigment product was confirmed by SEM. Characteristics of the resulting composite pigment product are listed as sample 1 in Table 1 below.

Example 2

2.4 kg of the milk of lime from Example 1 was treated as in Example 1 except that 110 ml of a 3.9% suspension of calcite nuclei with a BET of 42 $m^2$/g was added before the carbonating, and the amount of sodium silicate solution added was 220 g. Characteristics of the product are listed as sample 2 in Table 1.

Example 3

2.4 kg of the milk of lime from example 1 was treated as in Example 1 except that 110 ml of a 3.9% suspension of calcite nuclei with a BET of 42 $m^2$/g was added before the carbonating, the amount of sodium silicate solution added was 220 g and the speed of the propeller was set at approximately 935 rpm. Characteristics of the product are listed as sample 3 in Table 1.

Example 4

4.5 kg of the milk of lime from Example 1 was treated as in example 1 except that no water was added, the amount of sodium silicate solution added was 210 g and the speed of the propeller was set at approximately 935 rpm.

The reaction mixture was partly gelled. The gelled parts of the mixture were disintegrated by agitation after the reaction. Remaining lumps of gel were removed by the screening. Characteristics of the product are listed as sample 4 in Table 1.

Example 5

4.5 kg of the milk of lime from example 1 was treated as in Example 1 except that no water was added, 110 ml of a 3.9% suspension of calcite nuclei with a BET of 42 $m^2$/g was added before the carbonating, the amount of sodium silicate solution added was 420 g and the speed of the propeller was set at approximately 935 rpm.

The reaction mixture was partly gelled. The gelled parts of the mixture were disintegrated by agitation after the reaction. Remaining lumps of gel were removed by the screening. Characteristics of the product are listed as sample 5 in Table 1.

Example 6

The five samples prepared in the above Examples 1–5 were tested as fillers for paper in a dynamic sheet former study together with five comparative PCC samples. In Table 1, Samples 1–5 correspond to composite pigments made according to Examples 1–5, respectively. The comparative PCC samples, i.e. Samples 6–10, indicated in Table 1 were each made in the same manner as the pigment of Example 1 except that no sodium silicate solution was introduced during the carbonating procedure. The properties of the composite pigments of each of the ten samples are summarized in Table 1.

TABLE 1

| Sample number | % $SiO_2$ | MPS, Sedigraph, $\mu m$ | BET, $m^2/g$ | Zeta-potential, mV | MPS, Acoustosizer, $\mu m$ | Oil absorption, ml/100 g |
|---|---|---|---|---|---|---|
| 1 | 3.9% | 2.78 | 13.4 | −17.6 | 0.806 | 87.5 |
| 2 | 7.6% | 3.65 | 23.9 | −19.3 | 0.527 | 96.3 |
| 3 | 7.6% | 2.84 | 23.6 | −20.3 | 0.563 | 93.6 |
| 4 | 4.0% | 2.12 | 16.2 | −28 | 0.996 | 87.7 |
| 5 | 7.7% | 2.61 | 15.2 | −25 | 0.713 | 85.8 |
| 6 | 0 | 3.40 | 5.9 | 19.3 | 1.76 | 71.0 |
| 7 | 0 | 2.23 | 6.2 | 19.3 | 1.475 | 63.4 |
| 8 | 0 | 2.80 | 8.7 | 13.7 | 1.02 | 79.8 |
| 9 | 0 | 3.31 | 4.4 | 18.1 | 1.41 | 74.6 |
| 10 | 0 | 2.69 | 6.2 | 14 | 1.12 | 80.9 |

Paper sheets were made in normal manner on a dynamic sheet former from FiberTech, Sweden. The pulp was a 60:40 mix of long and short fibers beaten to a Shopper Riegler of 25. 2.5 kg/t wet end starch (Raisamyl 135) was added to the furnish. The retention system was a two-component polyacrylamid (Hydrocol® 1142, 250 g/t)+bentonite (Hydrocol® O 2.5 kg/t) retention system.

The sheets were prepared to three filler level targets: which contained 23, 25 and 28% filler based on the composite pigment solids. Results were interpolated to 24% filler level. The interpolated results, calculated from the measured properties of the DSF sheets, are given in Table 2.

TABLE 2

| Sample Number | Bulk, $cm^3/g$ | Scattering, $m^2/g$ | Permeability, $\mu m/Pa \cdot s$ | CD tensile index, kNm/g | CD Stiffness, mNm |
|---|---|---|---|---|---|
| 1 | 1.366 | 68.5 | 5.1 | 21.87 | 0.40 |
| 2 | 1.332 | 66.8 | 4.8 | 20.85 | 0.43 |
| 3 | 1.323 | 69.6 | 4.2 | 22.68 | 0.45 |
| 4 | 1.349 | 70.4 | 5.0 | 19.98 | 0.52 |
| 5 | 1.360 | 74.2 | 5.1 | 20.21 | 0.41 |
| 6 | 1.321 | 62.2 | 6.5 | 21.00 | 0.37 |
| 7 | 1.310 | 66.8 | 4.7 | 22.35 | 0.43 |
| 8 | 1.286 | 67.2 | 4.0 | 22.94 | 0.44 |
| 9 | 1.326 | 63.1 | 5.8 | 22.42 | 0.54 |
| 10 | 1.297 | 66.0 | 5.1 | 22.75 | 0.43 |

Figure 5:
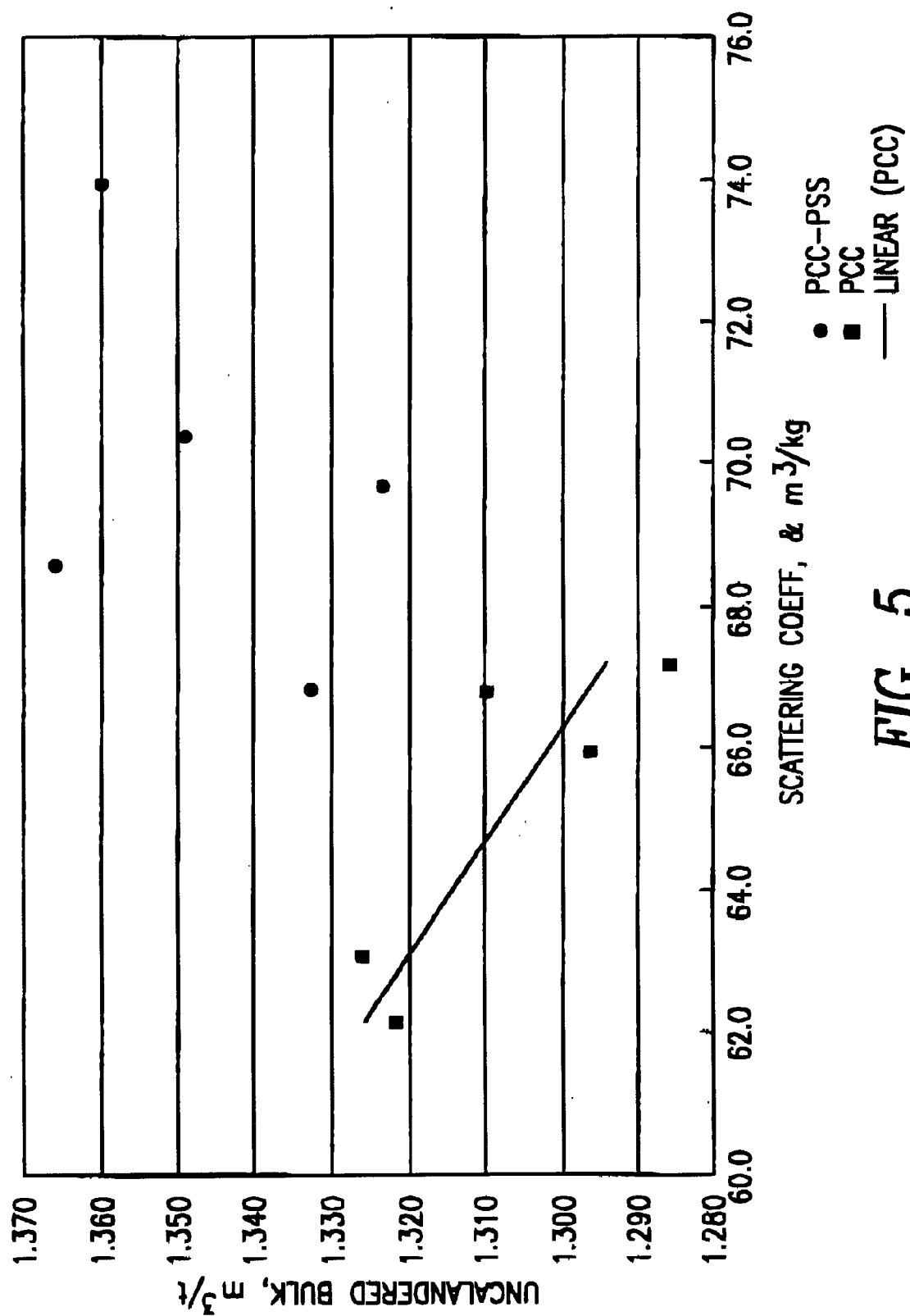
FIG. 5 is a graph comparing the bulk and scattering coefficient properties of paper sheets where some paper sheets were filled with composite precipitated calcium carbonate/silicate pigment made according to samples representing this invention and other paper sheets were filled with unmodified PCC pigment samples.
Figure 6:
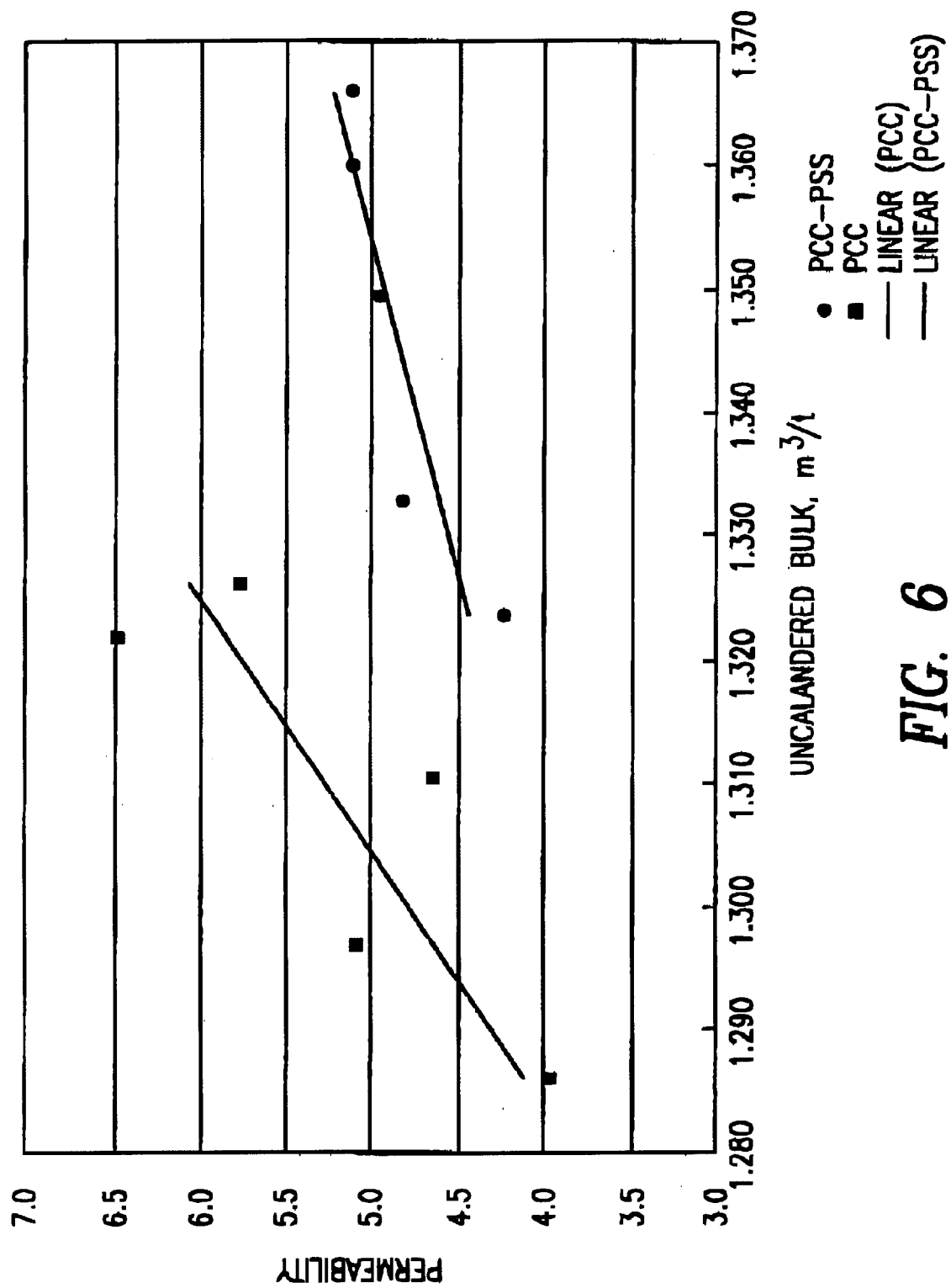
FIG. 6 is a graph comparing the air permeability and bulk properties of paper sheets where some were filled with composite precipitated calcium carbonate/silicate pigment made according to samples representing this invention and other paper sheets were filled with unmodified PCC pigment samples.

As shown graphically in FIG. 5, the paper sheets filled with composite PCC/silicate pigment according to this invention, i.e., samples 1–5 which are labelled in the FIGS. 5–6 as "♦<black diamond>PCC-PSS", demonstrated improved scattering and bulk as compared to the paper sheets filled with the unmodified PCC, i.e., samples 6–10 labelled in the FIGS. 5–6 as "■<black square>PCC", while FIG. 6 graphically demonstrates that the improvements in bulk (and scattering as shown in FIG. 5) was achieved without sacrificing (i.e., increasing) the air permeability. Reduced air permeability for paper is generally associated with improved printing properties.

Examples 7A–D and Comparative Examples 1 and 2

The scalability of the invention was studied using a pilot reactor. First, two PCC-PSS reactions (Examples 7A, 7B) and two PCC reactions (Comparative Examples 1, 2; "CE1" and "CE2", respectively) were carried out in a pilot reactor. The four reactions employed similar reaction parameters except that only Examples 7A and 7B included a step of adding water glass to the reaction mixture at a time when the conductivity began dropping.

More specifically, for each of the four runs, 50 kg of lime, which was a mixture of two lime types, 95% Lhoist, Rety and 5% Lhoist, Sorcy, both of France, was first reacted with 250 kg of water heated to 40° C. 25g $Na_2S_2O_3$ was added to the water before the addition of the lime.

Figure 7:
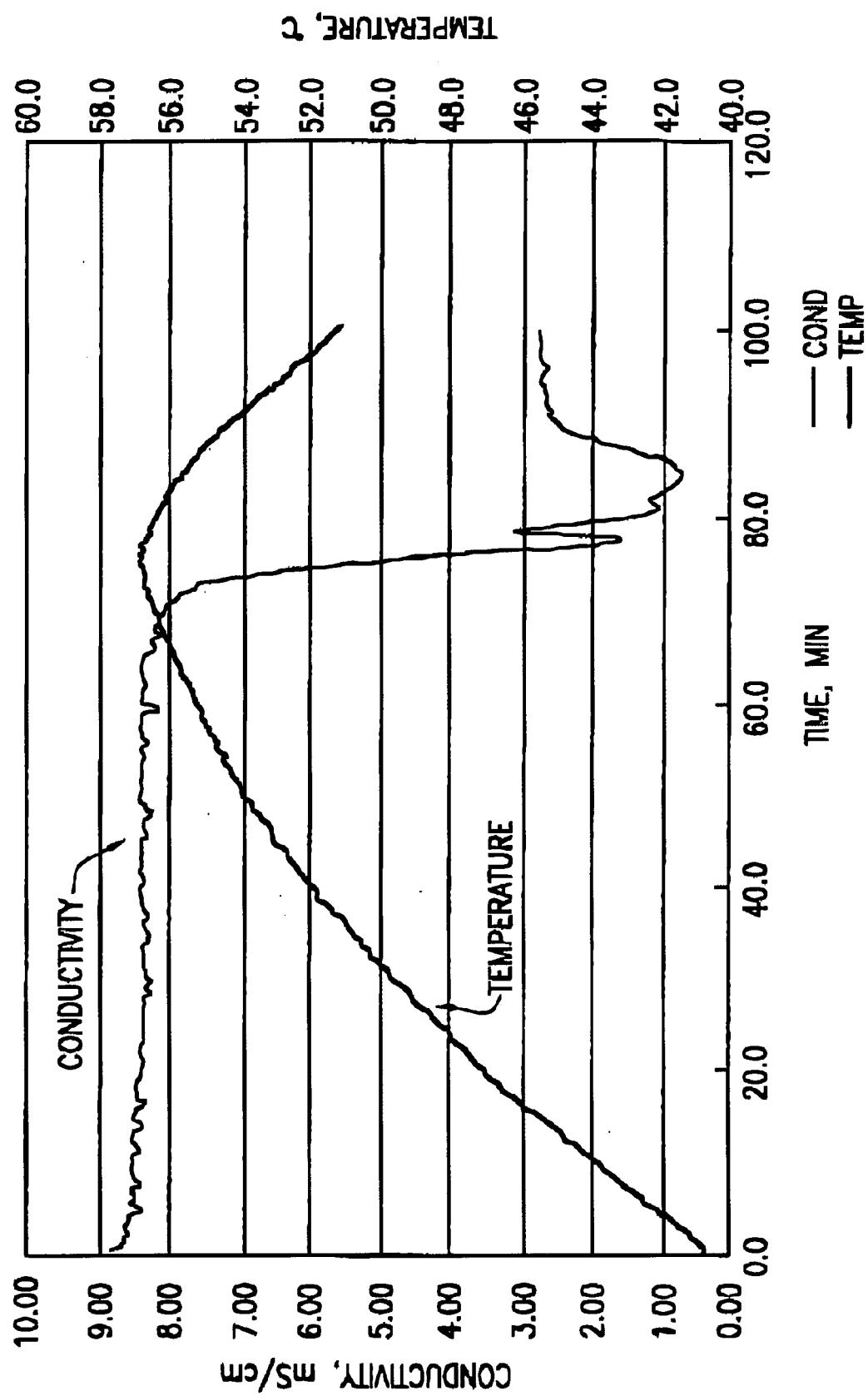
FIG. 7 is a graph showing the conductivity and reaction temperature as a function of reaction time for an aqueous reaction mixture in which a non-composite precipitated calcium carbonate pigment is made according to a comparative example.

The milk of lime was stirred for 30 minutes and then screened on a 200 $\mu m$ screen. The screened milk of lime was pumped to a pilot reactor. 200 L water was added and the temperature was adjusted to 40° C. Agitation speed was adjusted to 250 rpm, and 15 g sucrose was added to the milk of lime. A mixture of $CO_2$ and atmospheric air containing 20% $CO_2$ was injected at a flow rate of 90 $m^3/hr$. The reaction batches for Comparative Examples 1 and 2 were continued for 15 minutes after final conductivity was reached. The conductivity curve for the PCC reaction of Comparative Example 1 is shown in FIG. 7.

Figure 8:
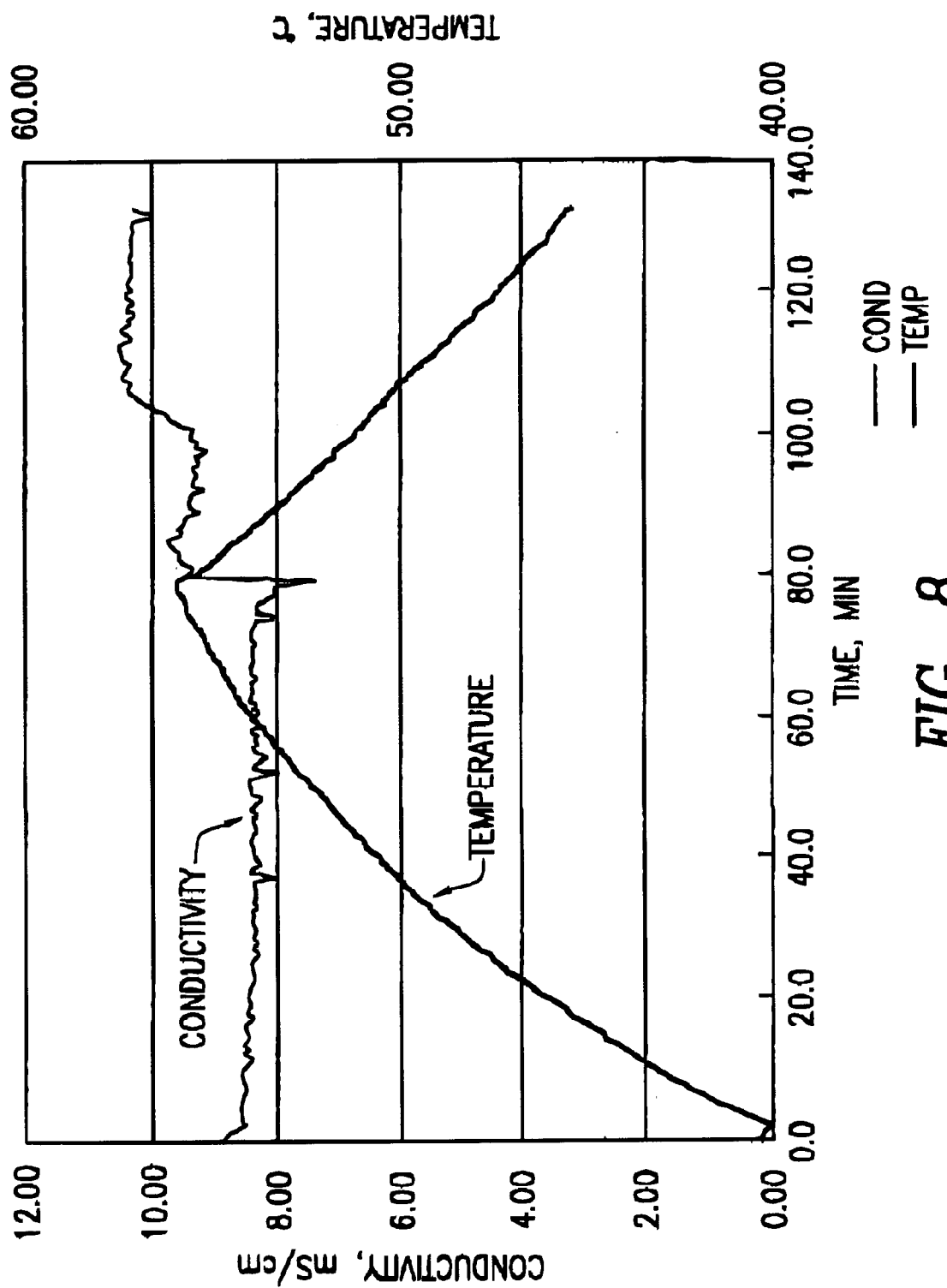
FIG. 8 is a graph showing the conductivity and reaction temperature as a function of reaction time for an aqueous reaction mixture in which a composite precipitated calcium carbonate pigment is made according to another example of this invention.
Figure 9A:
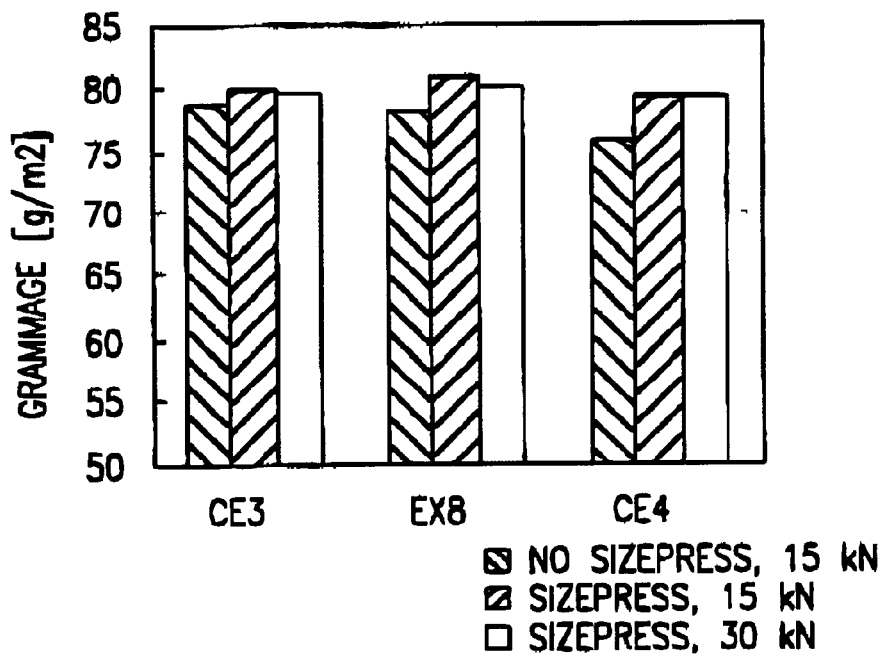
FIGS. 9A, 9B, 9C, 9D and 9E are graphs showing results obtained from measurements of the grammage, bulk, porosity, light scattering properties and CIE whiteness, respectively, of papers filled by composite pigments made according to this invention versus those made with comparative PCC pigments.
Figure 9B:
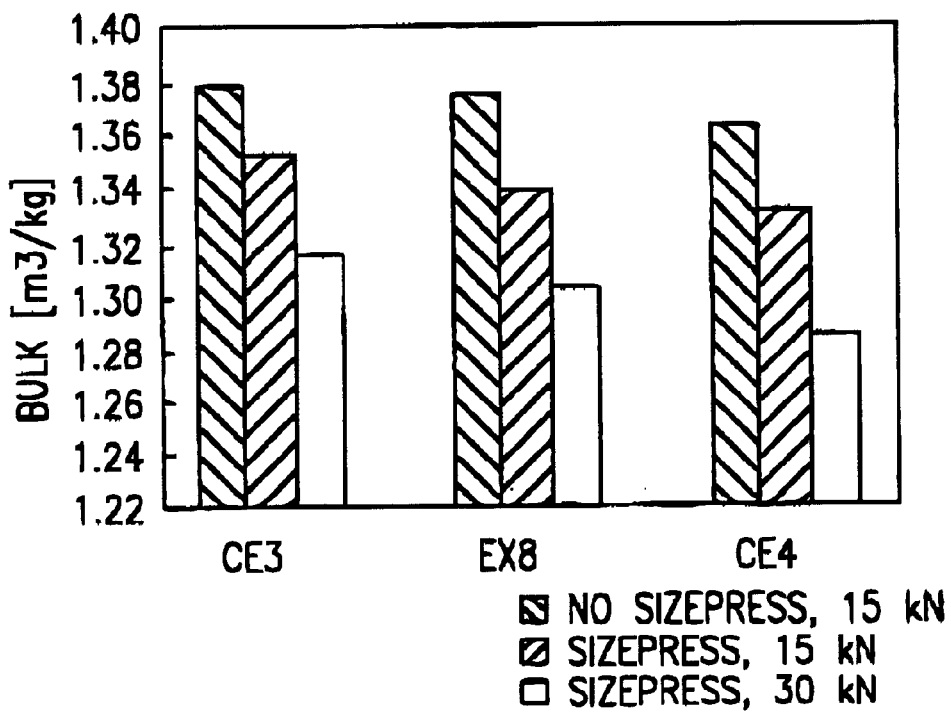
Figure 9C:
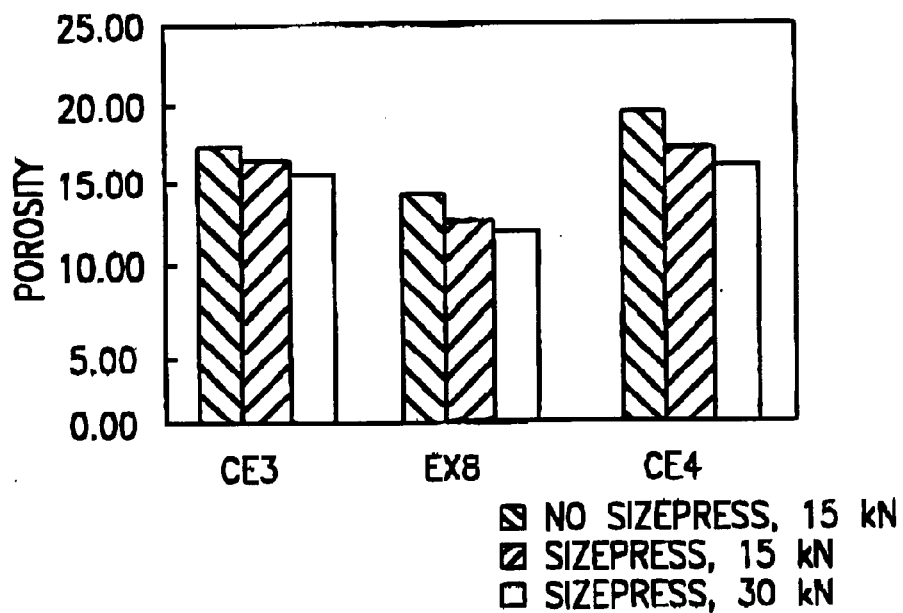
Figure 9D:
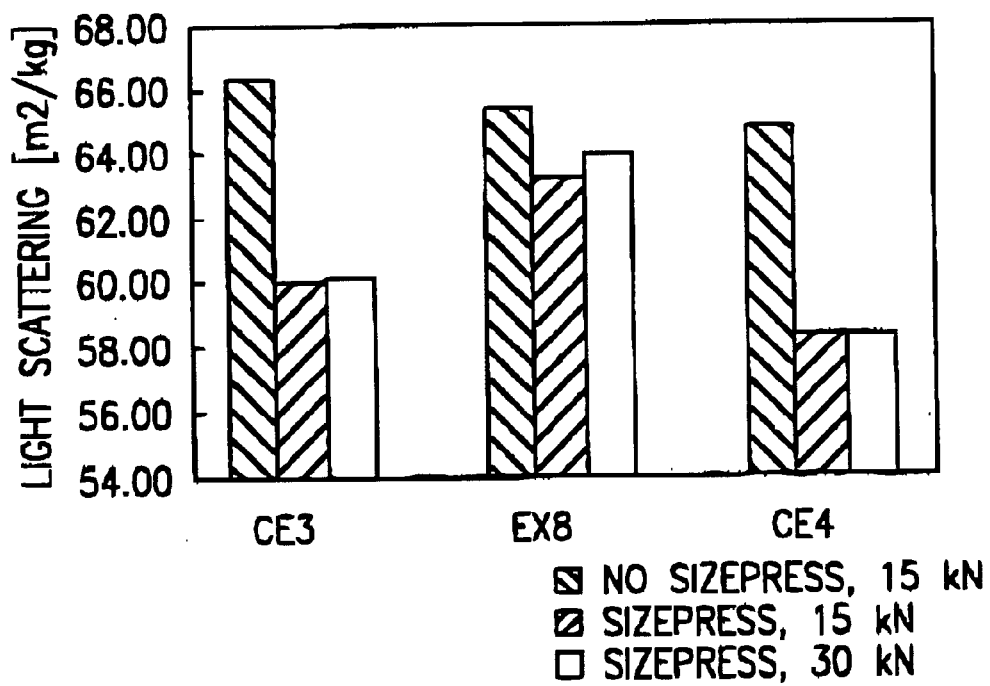
Figure 9E:
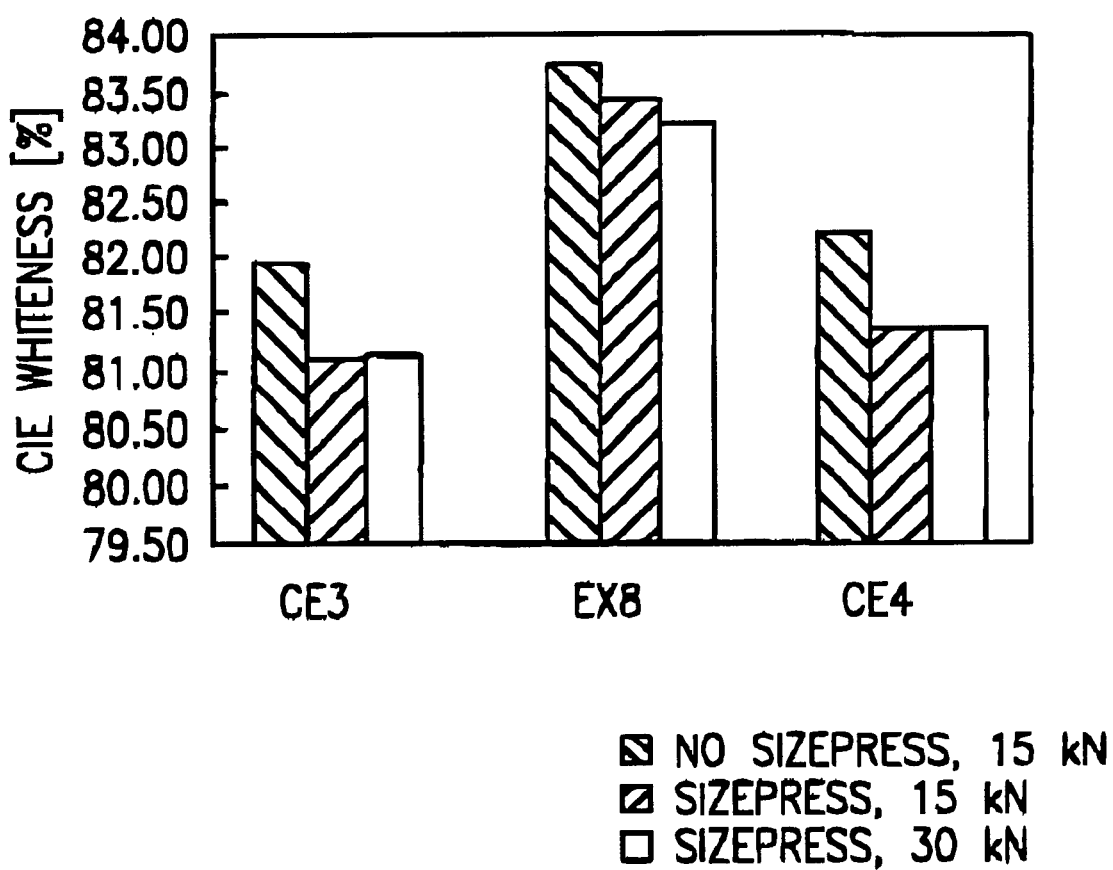

By contrast, in Examples 7A and 7B, 14 kg of a sodium silicate solution, Zeopol® 33 from Zeofinn OY, Finland, was added to the reactor at the time when the conductivity started to drop, such as shown in FIG. 8. This corresponded to 3.94 kg $SiO_2$ and 4.5% $SiO_2$ of the pigment respectively in Examples 7A and 7B. After the sodium silicate solution additions in Examples 7A and 7B, the reactions were continued for another 45 minutes. The conductivity curve for PCC-PSS synthesis reaction for Example 7B is shown in FIG. 8. The product composition, an aqueous slurry of the precipitated calcium carbonate/precipitated silicate composite, was screened on a 45 $\mu m$ mesh screen. The undersize (minus) portion was recovered as the pigment product composition, and the over size (plus) portion discarded. The properties of the pigment products were determined and the results are summarized in Table 3.

TABLE 3

| Run | CE1 | CE2 | 7A | 7B |
|---|---|---|---|---|
| solids, wt % | 17.3% | 16.0% | 16.4% | 17.5% |
| Sedigraph MPS, $\mu m$ | 2.77 | 2.83 | 2.58 | 2.60 |
| 75/25 | 1.62 | 1.64 | 1.63 | 1.70 |
| BET, $m^2/g$ | 6.1 | 5.2 | 10.8 | 11.9 |
| brightness, % | 95.3 | 95.4 | 95.4 | 95.2 |
| viscosity, mPA/s | 20 | 21 | 72 | 78 |
| % aragonite | 0 | 0 | 22 | 43 |

TABLE 3-continued

| Run | CE1 | CE2 | 7A | 7B |
|---|---|---|---|---|
| zetapotential mV | 11.1 | 10.7 | −20.1 | −20.0 |
| Acoustosizer MPS, μm | 1.16 | 1.01 | 0.67 | 0.67 |

The "75/25" values reported in Table 3 (and Table 4 herein) refer to so-called "slope" values, where the slope value is determined as the quotient value of the diameter value for which 75% of the pigment particles are less than (as the numerator), divided by the diameter value for which 25% of the pigment particles are less than (as the denominator), where the particle sizes are measured by a Sedigraph Particle Size Analyzer.

Comparison of the results of these studies with sample 1 in example 1 demonstrated that the inventive $CO_2$ PCC-PSS reaction could be scaled up in a facile and successful manner.

Example 8 and Comparative Examples 3 and 4

In Example 8, pilot paper machine trials were conducted using a 50/50 mixture of the pigments made in above Examples 7A and 7B. Comparative Example 3 (CE3) was a commercially available PCC obtained from J. M. Huber, Kaukopää Imatra plant, Finland. For Comparative Example 4 (CE4), pilot paper machine trials were carried out using a 50/50 mixture of the pigments made in the above-described Comparative Examples 1 and 2. The properties of pigment blend samples collected prior to performing the pilot paper machine trials were determined and the results are summarized in Table 4.

TABLE 4

| Example | 8 | CE3 | CE4 |
|---|---|---|---|
| MPS, μm | 2.60 | 2.25 | 2.68 |
| BET, m²/g | 8.6 | 5.3 | 5.9 |
| brightness, % | 95.3 | 95.5 | 95.4 |
| solids, % | 16.6 | — | 15.9 |
| 75/25 | 1.67 | — | 1.76 |
| viscosity, mPa/s | 25 | — | 15 |

Approximately 80 g/m² standard copy paper was produced on a pilot paper machine for each of Example 8 and Comparative Example 3 and 4. The pulp was a bleached chemical pulp consisting of 50% hardwood and 50% softwood, which was beaten to Schopper-Riegler 30. A conventional paper machine with a Fourdrinier forming section was used. The pH in the head-box was about 8.5. To accomplish this, two pigment filler levels were targeted at 24 and 27% for each tested sample. In addition, at each pigment filler level, a size press was used followed by calendering at pressures of 15 and 30 kN/m. The size press was turned off from 15 kN/m calendering giving a third test point. Results were interpolated to a 25.5% filler load. Thus, after interpolation to a constant filler load, three samples were obtained: surface sized 15 kN/m, surface sized 30 kN/m, and non-surface sized at 15 kN/m. 0.18% alkyl ketone dimer (AKD) sizing agent (based oven dry pulp), and 12 kg/ton cationic starch, degree of substitution 0.06, (Raisamyl 135) was added to the stock (2 kg for retention+10 kg for dry strength). 0.8 kg/ton colloidal silica (BMA 590), sold by Eka Nobel Ltd., was used as microparticle for retention. 3 kg/ton Basoplast ® (400DS), calculated as received per ton produced paper, was added to the surface size and the size concentration was 7%. The surface size used was a slightly cationic potato starch, Raisamyl 406. The paper machine speed was 80 m/min. The interpolated results obtained from measurements of the grammage, bulk, porosity (measured by PPS), light scattering properties, and CIE whiteness of the papers filled by the various pigments investigated here are depicted in FIGS. 9A, 9B, 9C, 9D, and 9E, respectively. The results demonstrated that paper filled with the inventive PCC-PSS pigment had good mechanical properties while also displaying improved optical properties.

The invention has been described with reference to certain preferred embodiments. However, as obvious variations thereon will become apparent to those skilled in the art, the invention is not to be considered as limited thereto.

For example, although illustrated in the examples for paper production, the inventive composite pigment also has utility for other and diverse applications such as a pigment for paints. Additionally, the inventive composite pigment, in dried solid particulate form, can be used as a thickener and/or cleaning agent in dentifrice compositions such as toothpastes, or as a conditioner for powders, or as a carrier for liquids or oils, to name a few examples.

What is claimed is:

1. A method for making a composite pigment, comprising the steps of:
    (a) providing lime mink comprising calcium hydroxide suspended in an aqueous medium;
    (b) inducing a calcium carbonate precipitation reaction by introducing carbon dioxide into the lime milk effective to precipitate calcium carbonate as a reaction product of the calcium hydroxide and the carbon dioxide;
    (c) introducing a soluble silicate compound into the aqueous medium at a time when the calcium carbonate precipitation reaction in step (b) has progressed to within approximately 90% to 100% of completion; and
    (d) introducing carbon dioxide into the aqueous medium containing said soluble silicate compound and precipitated calcium carbonate for a period of time effective to precipitate an insoluble silicon compound onto said precipitated calcium carbonate to provide a composite pigment, wherein the aqueous reaction medium has a maximum temperature variation during the silicate precipitation period of less than 20° C. during said period of time.

2. The method according to claim 1, further including the additional step of adjusting the temperature of said aqueous medium to at least 50° C. or higher after step (c) and before step (d).

3. The method according to claim 1, further including the additional step of adjusting the temperature of said aqueous medium to within the range of 70 to 90° C. after step (c) and before step (d).

4. The method according to claim 1, wherein said precipitated insoluble silicon compound is selected from the group consisting of amorphous silica, silicates, compound salts of silicates with calcium carbonate, and compound salts of silicates with magnesium carbonate, singly or in combinations thereof.

5. The method according to claim 1, wherein said composite pigment has a BET surface area of 5 to 25 m²/g.

6. The method according to claim 1, wherein a portion of said precipitated calcium carbonate is in the form of a calcite polymorph of calcium carbonate.

7. The method according to claim 1, wherein a portion of said precipitated calcium carbonate is in the form of an aragonite polymorph of calcium carbonate.

8. The method according to claim 1, wherein said precipitated calcium carbonate comprises a calcite polymorph of precipitated calcium carbonate, and said precipitated calcium carbonate comprises aggregates of calcium carbonate crystals formed by direct transformation of calcium hydroxide into calcium carbonate.

9. The method according to claim 1, wherein said precipitated calcium carbonate comprises a calcite polymorph of precipitated calcium carbonate, and said precipitated calcium carbonate comprises aggregates of calcium carbonate crystals formed by transformation of calcium hydroxide into calcium carbonate via an intermediate, basic calcium carbonate.

10. The method according to claim 1, wherein the soluble silicate compound added in step (c) is in an amount effective such that the resulting amount of insoluble silicon compound precipitated onto the calcium carbonate, calculated as % weight/weight of silica ($SiO_2$) relative to total weight of composite pigment product is in the range of 0.1 to 16%.

11. The method according to claim 1, wherein the soluble silicate compound added in step (c) is in an amount effective such that the resulting amount of insoluble silicon compound precipitated onto the calcium carbonate, calculated as % weight/weight of silica ($SiO_2$) relative to total weight of composite pigment product is in the range of 0.4 to 8%.

12. The method according to claim 1, wherein the soluble silicate compound comprises an alkali metal silicate.

13. A method according to claim 1, further including the additional steps of dewatering and drying to provide a dried, solid particulate form of said composite pigment.

14. A method for precipitation of at least one silicon compound selected from the group comprising amorphous silica and insoluble silicates, onto a calcitic precipitated calcium carbonate forming a composite pigment, wherein an aqueous solution of sodium silicate is added to an aqueous suspension of said calcitic precipitated calcium carbonate at a time near the end of the precipitation of the calcium carbonate followed by the precipitation of said sodium silicate as an insoluble silicon compound onto said calcitic precipitated calcium carbonate by introduction of a gas containing carbon dioxide, thereby forming said composite pigment, the amount of said sodium silicate added is in the range of 1 to 5.5% calculated as dry weight of sodium silicate relative to dry weight of the calcitic precipitated calcium carbonate, and said composite pigment has a BET surface area of 10–25 $m^2/g$.

* * * * *